United States Patent
Chono

(10) Patent No.: US 10,660,603 B2
(45) Date of Patent: May 26, 2020

(54) ULTRASOUND DIAGNOSTIC DEVICE

(71) Applicant: HITACHI, LTD., Tokyo (JP)

(72) Inventor: Tomoaki Chono, Tokyo (JP)

(73) Assignee: HITACHI, LTD., Tokyo (JP)

( * ) Notice: Subject to any disclaimer, the term of this patent is extended or adjusted under 35 U.S.C. 154(b) by 77 days.

(21) Appl. No.: 16/092,581

(22) PCT Filed: Mar. 30, 2017

(86) PCT No.: PCT/JP2017/013152
§ 371 (c)(1),
(2) Date: Oct. 10, 2018

(87) PCT Pub. No.: WO2017/179433
PCT Pub. Date: Oct. 19, 2017

(65) Prior Publication Data
US 2019/0125299 A1    May 2, 2019

(30) Foreign Application Priority Data
Apr. 13, 2016    (JP) .................... 2016-079955

(51) Int. Cl.
*G06T 7/12*    (2017.01)
*A61B 8/08*    (2006.01)
(Continued)

(52) U.S. Cl.
CPC .......... *A61B 8/0891* (2013.01); *A61B 8/0858* (2013.01); *A61B 8/14* (2013.01);
(Continued)

(58) Field of Classification Search
CPC combination set(s) only.
See application file for complete search history.

(56) References Cited

U.S. PATENT DOCUMENTS 5,485,831 A * 1/1996 Holdsworth .......... A61M 5/007
  600/431
6,817,982 B2 * 11/2004 Fritz .................... A61B 8/0858
  382/128
(Continued)

FOREIGN PATENT DOCUMENTS

| JP | 2005-118314 A | 5/2005 |
| JP | 2013-085694 A | 5/2013 |

(Continued)

OTHER PUBLICATIONS

International Search Report with English translation issued in corresponding application PCT/JP2017/013152 dated May 9, 2017.
(Continued)

*Primary Examiner* — Tsung Yin Tsai
(74) *Attorney, Agent, or Firm* — Foley & Lardner LLP

(57) ABSTRACT

A streak image enhancing unit subjects an ultrasound image representing a blood vessel to processing using a two-dimensional filter that is longer in the long axis direction of the blood vessel than in the short axis direction thereof so as to enhance a streak image corresponding to the long axis direction. A trace line candidate extracting unit extracts from the ultrasound image with the enhanced streak image a plurality of trace line candidates on the basis of the output values of the two-dimensional filter. A trace line selecting unit selects two trace lines corresponding to the inner boundary of the tunica intima and the boundary between the tunica media and the tunica externa of the blood vessel out of the plurality of trace line candidates on the basis of an evaluation value relating to continuity acquired for each trace candidate.

16 Claims, 10 Drawing Sheets

(51) Int. Cl.
*A61B 8/14* (2006.01)
*G06T 7/181* (2017.01)
*G06T 7/13* (2017.01)
*G06T 7/60* (2017.01)

(52) U.S. Cl.
CPC .......... *A61B 8/5223* (2013.01); *A61B 8/5269* (2013.01); *G06T 7/12* (2017.01); *G06T 7/13* (2017.01); *G06T 7/181* (2017.01); *G06T 7/60* (2013.01); *G06T 2207/10132* (2013.01); *G06T 2207/20024* (2013.01); *G06T 2207/20192* (2013.01); *G06T 2207/30101* (2013.01)

(56) References Cited

U.S. PATENT DOCUMENTS

| | | | | |
|---|---|---|---|---|
| 6,835,177 B2* | 12/2004 | Fritz | ................. | A61B 5/02007 382/128 |
| 7,569,016 B2* | 8/2009 | Watanabe | .......... | A61B 5/02007 382/128 |
| 7,686,764 B2* | 3/2010 | Watanabe | .......... | A61B 5/02007 600/443 |
| 7,727,153 B2* | 6/2010 | Fritz | ................. | A61B 5/02007 600/449 |
| 7,959,572 B2* | 6/2011 | Ishihara | ............. | A61B 5/02007 382/128 |
| 8,079,958 B2* | 12/2011 | Satoh | ................ | A61B 5/02007 382/128 |
| 8,313,437 B1* | 11/2012 | Suri | ..................... | A61B 8/0858 382/128 |
| 8,485,975 B2* | 7/2013 | Suri | ..................... | A61B 8/0858 600/443 |
| 8,532,360 B2* | 9/2013 | Suri | ....................... | A61B 8/483 382/131 |
| 8,708,914 B2* | 4/2014 | Suri | ..................... | G06T 7/0012 382/128 |
| 9,579,084 B2* | 2/2017 | Miyachi | ............... | A61B 8/0858 |
| 9,629,615 B1* | 4/2017 | Tavakoli | ................ | G06T 7/269 |
| 2007/0149877 A1* | 6/2007 | Oshiki | .............. | A61B 5/02007 600/427 |
| 2012/0083698 A1 | 4/2012 | Chono | | |
| 2014/0334706 A1* | 11/2014 | Toma | ................... | A61B 8/0883 382/131 |
| 2015/0272541 A1 | 10/2015 | Hyuga | | |

FOREIGN PATENT DOCUMENTS

| | | |
|---|---|---|
| JP | 2013-111443 A | 6/2013 |
| JP | 5713896 B2 | 5/2015 |
| JP | 2015-198714 A | 11/2015 |
| WO | WO-2017179433 A1 * 10/2017 | ............... G06T 7/13 |

OTHER PUBLICATIONS

International Preliminary Report Form PCT/IB326 and Form PCT/IB338 issued in the corresponding International Application No. PCT/JP2017/013152.

* cited by examiner

ULTRASOUND DIAGNOSTIC DEVICE

TECHNICAL FIELD

The present disclosure relates to an ultrasound diagnostic apparatus, and in particular to an ultrasound diagnostic apparatus which diagnoses a blood vessel.

BACKGROUND

An ultrasound diagnostic apparatus is an apparatus which forms an ultrasound image based on reception data obtained by transmitting and receiving ultrasound, and displays the formed ultrasound image. In general, the ultrasound diagnostic apparatus has a plurality of operation modes (such as a B mode, a Doppler mode, etc.). Further, there is known an ultrasound diagnostic apparatus which has a plurality of measurement functions. An example of such a measurement function is a function of blood vessel measurement, and, for example, an IMT measurement of ultrasound is a representative example of blood vessel measurement.

The IMT measurement is a measurement targeted to a blood vessel such as, for example, a carotid artery, and is targeted to an Intima-Media Thickness of a blood vessel wall. The blood vessel wall has a three-layer structure including an intima, a media, and an adventitia, viewed in that order from the side of a bloodstream. In the IMT measurement, a thickness of a combined structure of the intima and the media (intima-media thickness, or IMT) is measured.

For example, Patent Document 1 discloses an invention related to the IMT measurement by an ultrasound diagnostic apparatus. Specifically, Patent Document 1 discloses an invention in which a region of interest including a blood vessel in an ultrasound image is divided into three regions including an inner cavity region of the blood vessel, an intima-media region, and an adventitia region by an inner cavity side dividing line and an adventitia side dividing line; an inner cavity side boundary is extracted in a range limited to the inner cavity side from the inner cavity side dividing line; an adventitia side boundary is extracted in a range limited to the adventitia side from the adventitia side dividing line; and the intima-media thickness is measured based on a distance between the inner cavity side boundary and the adventitia side boundary.

CITATION LIST

Patent Literature

Patent Document 1: JP 5713896 B

SUMMARY

Technical Problem

The invention of Patent Document 1 is an epoch-making invention which can suppress influences of noise in a boundary extraction operation of the IMT measurement. The present inventors have researched and developed a further improvement of the epoch-making invention.

An advantage of the present disclosure lies in provision of an improved technique for identifying a tunica boundary of a blood vessel in the ultrasound image.

Solution to Problem

According to one aspect of the present disclosure, there is provided an ultrasound diagnostic apparatus comprising: an enhancement processor that enhances, in an ultrasound image showing a cross section of a blood vessel, a streak image corresponding to a long-axis direction of the blood vessel by a process using a two-dimensional filter which is longer in the long-axis direction than a short-axis direction of the blood vessel; a candidate extractor that extracts a plurality of trace line candidates which are candidates of a tunica boundary of the blood vessel in the ultrasound image in which the streak image is enhanced, based on an output value of the two-dimensional filter; and a boundary selector that selects two trace lines corresponding to an intima inner side boundary and a media-adventitia boundary of the blood vessel from among the plurality of trace line candidates, based on an evaluation value related to continuity, obtained for each of the trace line candidates.

In an ultrasound image showing a cross section of a blood vessel, an intima inner side boundary of the blood vessel (boundary between the bloodstream and the intima) and the media-adventitia boundary (boundary between the media and the adventitia) have relatively high brightnesses. Thus, these tunica boundaries (the intima inner side boundary and the media-adventitia boundary) can be identified based on a brightness difference with a peripheral brightness, for example. However, in the ultrasound image, noise such as a speckle also has a high brightness, and becomes an obstruction for identifying the tunica boundary.

In consideration of this, for example, in order to reduce the influence of the noise, the ultrasound diagnostic apparatus of the above-described structure enhances a streak image corresponding to the long-axis direction, by a process using a two-dimensional filter which is longer in the long-axis direction than a short-axis direction of the blood vessel. Because the tunica boundary of the blood vessel (the intima inner side boundary and the media-adventitia boundary) is a streak-form image approximately continuous in the long-axis direction, first, the streak image which is a candidate for the tunica boundary is enhanced. Because the two-dimensional filter is longer in the long-axis direction than in the short-axis direction, the streak image corresponding to the long-axis direction is more actively enhanced. With this process, the influence of noise or the like is relatively reduced.

In addition, the ultrasound diagnostic apparatus of the above-described structure extracts a plurality of trace line candidates which are candidates of the tunica boundary of the blood vessel in the ultrasound image in which the streak image is enhanced. Because the streak image corresponding to the long-axis direction is enhanced and the influence of the noise or the like is relatively reduced, an extraction precision for the plurality of trace line candidates which are candidates for the tunica boundary along the long-axis direction can be improved.

Further, according to the ultrasound diagnostic apparatus of the above-described structure, even if a trace line candidate different from the tunica boundary is included in the plurality of extracted trace line candidates, two trace lines corresponding to the intima inner side boundary and the media-adventitia boundary are selected based on an evaluation value related to continuity, obtained for each of the trace line candidates. For example, from the plurality of trace line candidates, two trace line candidates having relatively superior continuity are selected as two trace lines corresponding to the intima inner side boundary and the media-adventitia boundary.

In this manner, according to the ultrasound diagnostic apparatus of the above-described structure, two trace lines corresponding to the intima inner side boundary and the media-adventitia boundary are selected by enhancement of the streak image in the ultrasound image using the two-dimensional filter, extraction of a plurality of trace line candidates in the ultrasound image in which the streak image is enhanced, and selection based on the evaluation value related to the continuity, obtained for each of the trace line candidates. Therefore, in the ultrasound image showing the cross section of the blood vessel, it becomes possible to identify two trace lines corresponding to the intima inner side boundary and the media-adventitia boundary of the blood vessel with a very high level of precision. For example, by executing the IMT measurement using two trace lines thus identified, it becomes possible to dramatically improve the precision of the IMT measurement.

According to another aspect of the present disclosure, the enhancement processor enhances, by a process using the two-dimensional filter which is tilted at a plurality of angles with respect to the long-axis direction of the blood vessel, the streak image corresponding to the plurality of angles.

According to another aspect of the present disclosure, a length of the two-dimensional filter in the short-axis direction is shorter than a distance from the intima inner side boundary of the blood vessel to the media-adventitia boundary According to another aspect of the present disclosure, the candidate extractor identifies, in the ultrasound image in which the streak image is enhanced, a plurality of maxima pixels in which the output value of the two-dimensional filter is a maximum, and connects a plurality of the maxima pixels which are in an adjacent relationship, to form each of the trace line candidates.

According to another aspect of the present disclosure, the boundary selector sets, as the evaluation value and for each of the trace line candidates, an accumulated value in which the output values of the two-dimensional filter related to a plurality of pixels of the trace line candidate are accumulated, and selects, from among the plurality of trace line candidates, two trace line candidates from the largest of the accumulated value as two trace lines corresponding to the intima inner side boundary and the media-adventitia boundary of the blood vessel.

According to another aspect of the present disclosure, the ultrasound diagnostic apparatus calculates a distance between the two selected trace lines, and searches, in a search region including a position distanced from one trace line of the two trace lines toward a side of the other trace line by the distance, at least one trace line candidate to be added to the other trace line from among the plurality of trace line candidates.

Advantageous Effects of Invention

According to the present disclosure, an improved technique for identifying the tunica boundary of the blood vessel in the ultrasound image is provided. For example, according to a desirable configuration of the present disclosure, in the ultrasound image showing the cross section of the blood vessel, two trace lines corresponding to the intima inner side boundary and the media-adventitia boundary of the blood vessel can be identified with a very high level of precision.

DESCRIPTION OF EMBODIMENTS

Figure 1:
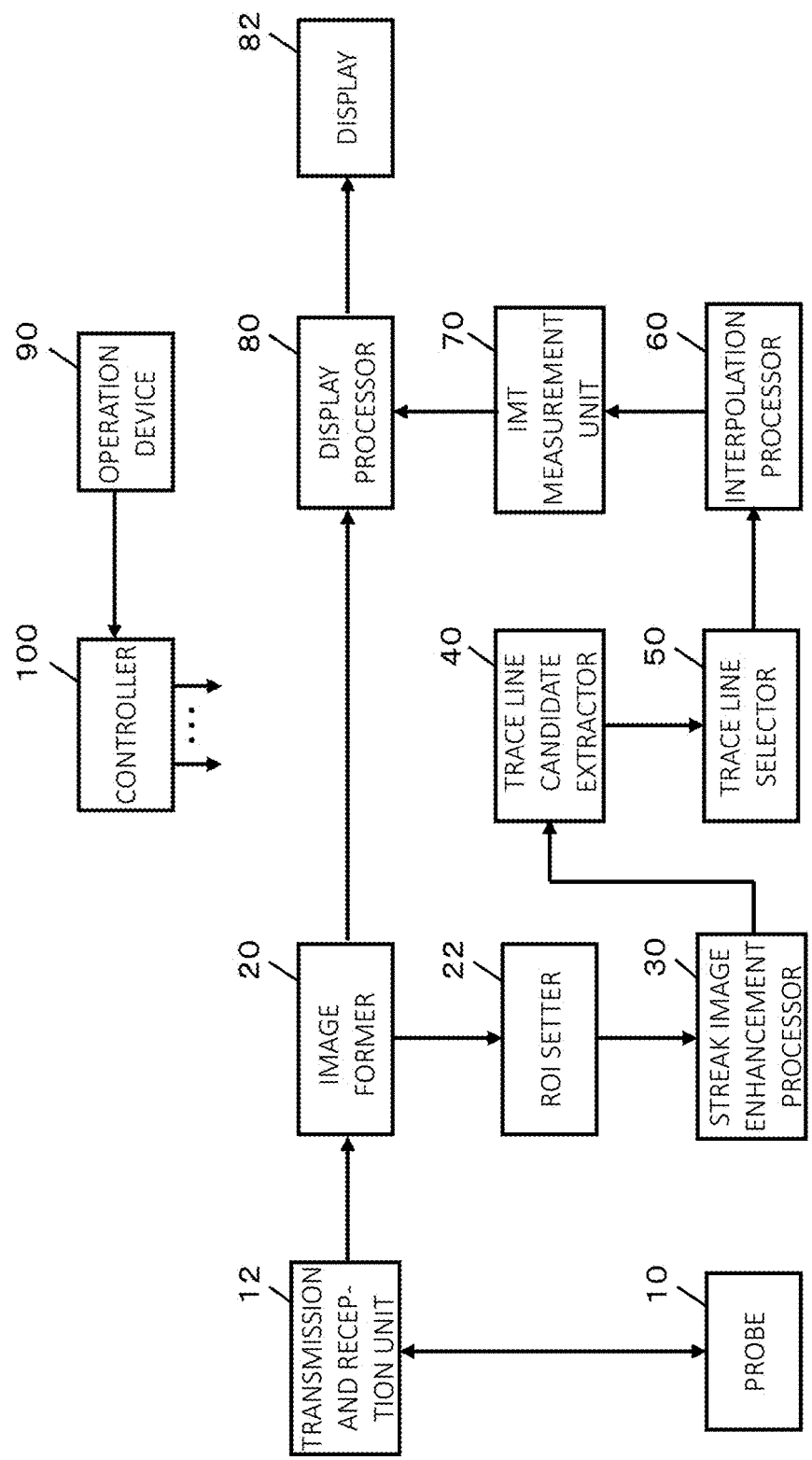
FIG. 1 is a diagram showing a specific example of an ultrasound diagnostic apparatus desirable in the present disclosure.

FIG. 1 is a diagram showing a specific example of an ultrasound diagnostic apparatus according to an embodiment of the present disclosure. The ultrasound diagnostic apparatus of FIG. 1 has a function of an IMT (Intima-Media Thickness) measurement of a blood vessel. A probe 10 is an ultrasound probe which transmits and receives ultrasound to and from a diagnosis region including the blood vessel (for example, a carotid artery) which is a target of the IMT measurement. The probe 10 comprises a plurality of transducer elements. The plurality of transducer elements are electrically controlled to be scanned, for example, to scan an ultrasound beam in a space including the diagnosis target. The probe 10 is, for example, held by a user (inspector) such as a doctor, an inspection technician, or the like, and is used in contact with a body surface of a subject. In the IMT measurement targeted to the carotid artery, as the probe 10, for example, a linear ultrasound probe (linear probe) is desirable. Alternatively, according to the measurement target and the measurement contents, a probe 10 of a type such as a convex type or a sector type may be used.

A transmission and reception unit 12 outputs a transmission signal corresponding to each of the plurality of transducer elements of the probe 10, to form a transmission beam of ultrasound, and scans the transmission beam. In addition, the transmission and reception unit 12 applies a phasing addition process or the like on a reception signal obtained from each of the plurality of the transducer elements of the probe 10, to form a reception beam corresponding to the scanned transmission beam, and outputs echo data (reception signal) obtained along the reception beam. In other words, the transmission and reception unit 12 has functions of a transmission beam former and of a reception beam former. Alternatively, the echo data (reception signal) may be obtained using a transmission and reception technique such as transmission aperture synthesis.

An image former 20 forms data of an ultrasound image (cross-sectional data) based on the reception signal of the ultrasound obtained from within a scanning plane. Specifically, the cross-sectional data is formed based on line data of a plurality of lines corresponding to a plurality of ultrasound beams formed within the scanning plane by the scanning. The image former 20 forms the cross-sectional data for a B mode image showing a long-axis cross section of the blood vessel by applying, for example, a wave detection process, a filter process, an AD conversion process, or the like, on the reception signal of the ultrasound. Alternatively, the wave detection process, the filter process, the A/D conversion process, or the like on the reception signal of the ultrasound may be executed at the transmission and reception unit 12.

An ROI setter 22 sets a region of interest (ROI) in image data of the ultrasound image formed by the image former 20. The ROI setter 22 sets, for example, a quadrangular region of interest showing a measurement range of the IMT measurement in the image data of the long-axis cross section of the blood vessel. A position in the image where the region of interest is to be set is determined, for example, by a user such as the doctor or the inspection technician operating an operation device 90. In addition, a size of the region of interest may be fixed, or may be changeable by the user operating the operation device 90.

A streak image enhancement processor 30 enhances a streak image corresponding to the long-axis direction in the ultrasound image showing the long-axis cross section of the blood vessel. A trace line candidate extractor 40 extracts a plurality of trace line candidates which are candidates for a tunica boundary of the blood vessel, in the ultrasound image in which the streak image is enhanced. A trace line selector 50 selects two trace lines corresponding to an intima inner side boundary and a media-adventitia boundary of the blood vessel from among a plurality of trace line candidates, based on an evaluation value related to continuity, obtained for each of the trace line candidates. An interpolation processor 60 executes an interpolation process on the trace line. The processes executed by the units from the streak image enhancement processor 30 to the interpolation processor 60; that is, the process for identifying the intima inner side boundary and the media-adventitia boundary of the blood vessel in the long-axis cross section of the blood vessel, will be described in more detail later.

An IMT measurement unit 70 calculates a measurement value of the IMT based on the intima inner side boundary and the media-adventitia boundary identified by the processes from the streak image enhancement processor 30 to the interpolation processor 60. In the IMT measurement, the intima-media thickness (IMT) is measured, which is a thickness of a combined structure of the intima and the media of a blood vessel wall of the blood vessel which is the measurement target.

The IMT measurement unit 70 measures the IMT in the region of interest (ROI) for the IMT measurement. The region of interest is set, for example, for a posterior wall of the blood vessel, and the IMT measurement unit 70 calculates, as the IMT measurement value of the posterior wall, a distance between the intima inner side boundary and the media-adventitia boundary, based on the intima inner side boundary (boundary between the bloodstream and the intima) identified in the posterior wall of the blood vessel in the region of interest, and the media-adventitia boundary (boundary between the media and the adventitia) identified in the same posterior wall. For example, an average of the distance between the intima inner side boundary and the media-adventitia boundary in the region of interest is calculated as the IMT measurement value. Alternatively, the region of interest may be set for an anterior wall of the blood vessel, and the IMT of the anterior wall may be measured. Further alternatively, the region of interest may be set for both the anterior and posterior walls, and the IMT measurement values for both the anterior and posterior walls may be calculated.

A display processor 80 forms a display image for the IMT measurement based on the cross-sectional data (image data of the ultrasound image) obtained from the image former 20 and the IMT measurement value obtained from the IMT measurement unit 70. The display image formed by the display processor 80 is displayed on a display 82.

A controller 100 comprehensively controls the ultrasound diagnosis apparatus of FIG. 1. In the comprehensive control by the controller 100, instructions received from the user such as the doctor or the inspection technician through the operation device 90 are also reflected.

Of the structures shown in FIG. 1 (portions to which the reference numerals are assigned), the transmission and reception unit 12, the image former 20, the ROI setter 22, the streak image enhancement processor 30, the trace line candidate extractor 40, the trace line selector 50, the interpolation processor 60, the IMT measurement unit 70, and the display processor 80 can be realized using hardware such as, for example, an electric or electronic circuit, a processor, or the like, and in realization of these structures, a device such as a memory may be used as necessary. Alternatively, at least a portion of the functions corresponding to the above-described units may be realized by a computer. That is, at least a portion of the functions corresponding to the above-described units may be realized by cooperation of hardware such as a CPU, a processor, and a memory, and software (program) which defines an operation of the CPU, and the processor.

A desirable specific example of the display 82 is a liquid crystal monitor or the like. The operation device 90 can be realized, for example, by at least one of a mouse, a keyboard, a trackball, a touch panel, and other switches. The controller 100 may be realized, for example, by cooperation of hardware such as the CPU, the processor, and the memory, and software (program) which defines an operation of the CPU and the processor.

The overall structure of the ultrasound diagnostic apparatus of FIG. 1 has been described. Next, a process for identifying tunica boundaries (the intima inner side boundary and the media-adventitia boundary) realized by the ultrasound diagnostic apparatus of FIG. 1 will be described in detail. The structures (portions) shown in FIG. 1 will be described with the reference numerals assigned in FIG. 1.

Figure 2:
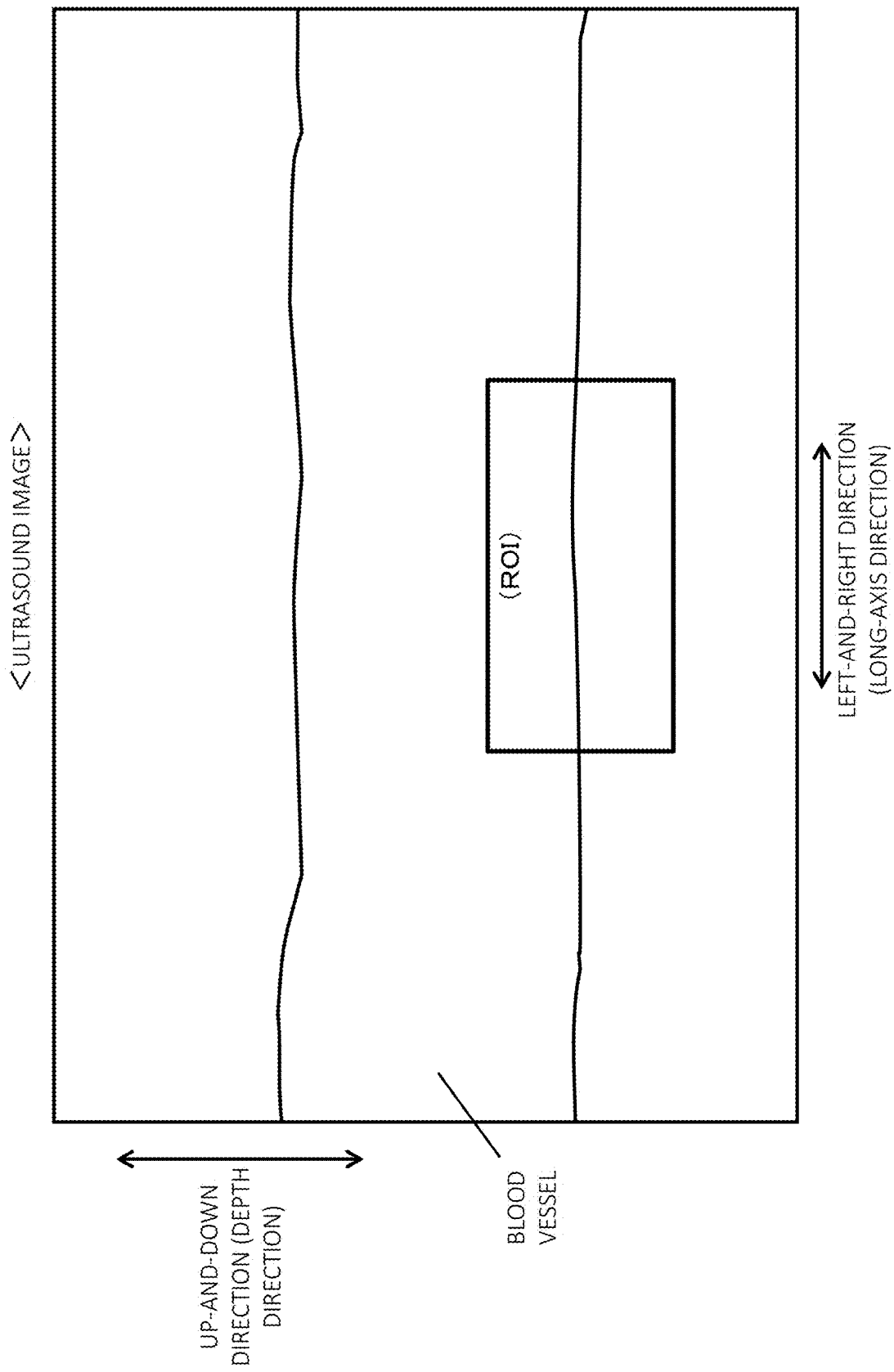
FIG. 2 is a diagram showing a specific example of an ultrasound image used for IMT measurement.

FIG. 2 is a diagram showing a specific example of an ultrasound image used in the IMT measurement. The ultrasound image of FIG. 2 is a specific example of image data (cross-sectional data) formed by the image former based on echo data (reception signal) obtained using the probe 10 of the linear scanning type. The image former 20 forms image data of the ultrasound image for each frame.

The ultrasound image of FIG. 2 shows a cross section of a blood vessel (for example, the carotid artery). In the IMT measurement, an ultrasound image is desirable which is formed such that the long-axis direction of the blood vessel is set to a left-and-right direction of the image (lateral direction). The ultrasound image is formed based on the echo data (reception signal) corresponding to the plurality of ultrasound beams having an up-and-down direction of the image as a beam direction (depth direction).

FIG. 2 shows a region of interest (ROI) which is set in the ultrasound image by the ROI setter 22. In the specific example shown in FIG. 2, a quadrangular (rectangular) region of interest (ROI) is set for the posterior wall of the blood vessel.

The streak image enhancement processor 30 enhances a streak image corresponding to the long-axis direction by a process using a two-dimensional filter which is longer in the long-axis direction of the blood vessel than in the short-axis direction, in the region of interest (ROI) which is set in the ultrasound image showing the long-axis cross section of the blood vessel. The two-dimensional filter is desirably a filter which reduces a responsiveness to a fine brightness change such as the noise, and increases a responsiveness to a horizontally long shape; that is, a shape long in the long-axis direction, so that the filter can enhance the horizontally long streak image while suppressing the influences of the noise or the like.

Figure 3:
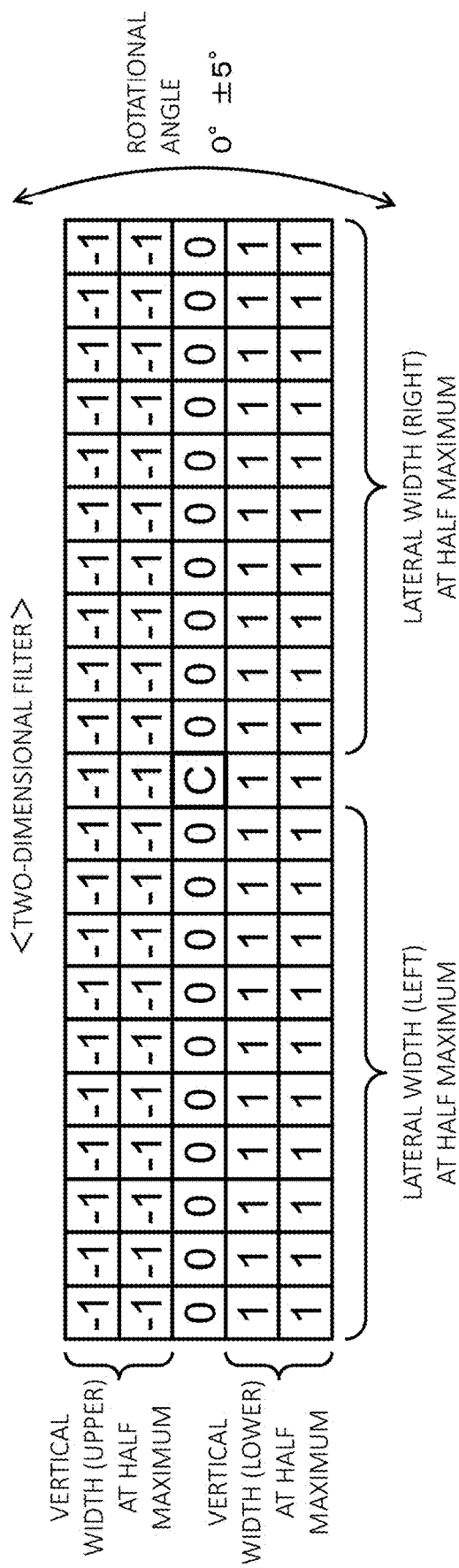
FIG. 3 is a diagram showing a specific example of a two-dimensional filter.

FIG. 3 is a diagram showing a specific example of the two-dimensional filter. FIG. 3 shows a two-dimensional filter which is based on a Sobel filter, and in which a lateral width (width in the left-and-right direction of FIG. 2), a vertical width (width in the up-and-down direction of FIG. 2), and an angle of the filter can be adjusted.

In FIG. 3, the two-dimensional filter has a window represented by a plurality of squares two-dimensionally arranged in the lateral direction (long-axis direction of the blood vessel) and the vertical direction (short-axis direction of the blood vessel), with a numerical value in each square, (−1, 0, 1), representing a filter coefficient. Each square is correlated to each pixel in the image. A filter coefficient of a center position (C) of the two-dimensional filter is 0 (zero). A pixel value of the pixel corresponding to a position of each square of the two-dimensional filter is multiplied by a filter coefficient, (−1, 0, 1), corresponding to the square, and the products of all squares of the two-dimensional filter are added, to obtain a filter output value related to the pixel corresponding to the center position (C).

In the specific example of FIG. 3, a lateral width at half maximum of the two-dimensional filter is, for example, desirably about 1.0 mm (about a few tens of pixels), and a left lateral width at half maximum and a right lateral width at half maximum are desirably the same length. Further, a vertical width at half maximum of the two-dimensional filter is, for example, desirably about 0.1 mm (about a few pixels), and an upper vertical width at half maximum and a lower vertical width at half maximum are desirably the same length.

Moreover, in the specific example of FIG. 3, the two-dimensional filter is tilted at a plurality of angles with respect to the long-axis direction of the blood vessel. Specifically, with the center position (C) of the two-dimensional filter as a center of rotation, the two-dimensional filter is tilted at, for example, three rotational angles, 0° and ±5° with respect to the long-axis direction (left-and-right direction of FIG. 2) of the blood vessel. With this configuration, three filter output values related to the pixel corresponding to the center position (C) of the two-dimensional filter are obtained, and a total of the three filter output values is set as a final filter output value. Alternatively, a maximum value of the filter output values corresponding to the three rotational angles may be output as the final filter output value. With regard to the rotational angles of the two-dimensional filter, it is desirable that the angle is within 10° in absolute value. Further, the number of angles is not limited to three, and may be, for example, two, or four or more.

The parameters related to the two-dimensional filter (the lateral width at the half maximum, the vertical width at the half maximum, and the rotational angle) are desirably determined based on experiments, for example, so that the trace line candidates extracted by the trace line candidate extractor 40 later are extracted at a maximum possible distance without disconnection at an eight-nearby connection. A vertical length (a total length in the vertical direction) of the two-dimensional filter is desirably set to a length in which not both the intima and the media of the blood vessel are included.

The streak image enhancement processor 30 obtains filter output values of all pixels in the region of interest (ROI) by applying the two-dimensional filter corresponding to the three angles on each of the pixels in the region of interest (ROI). For example, the two-dimensional filter is rotated at five angles at a position of each pixel to be processed, to calculate a filter output value for each angle. Alternatively, three two-dimensional filters may be prepared in advance, corresponding to the three angles, and the three two-dimensional filters may be applied to each pixel to be processed, to calculate the filter output value. With this process, the streak image corresponding to the long-axis direction of the blood vessel is enhanced. Because the two-dimensional filter corresponding to the three angles is used, for example, a streak image corresponding to a tunica surface (tunica boundary) having a very small angle (0° and ±5°) with respect to the long-axis direction can also be enhanced.

Figure 4:
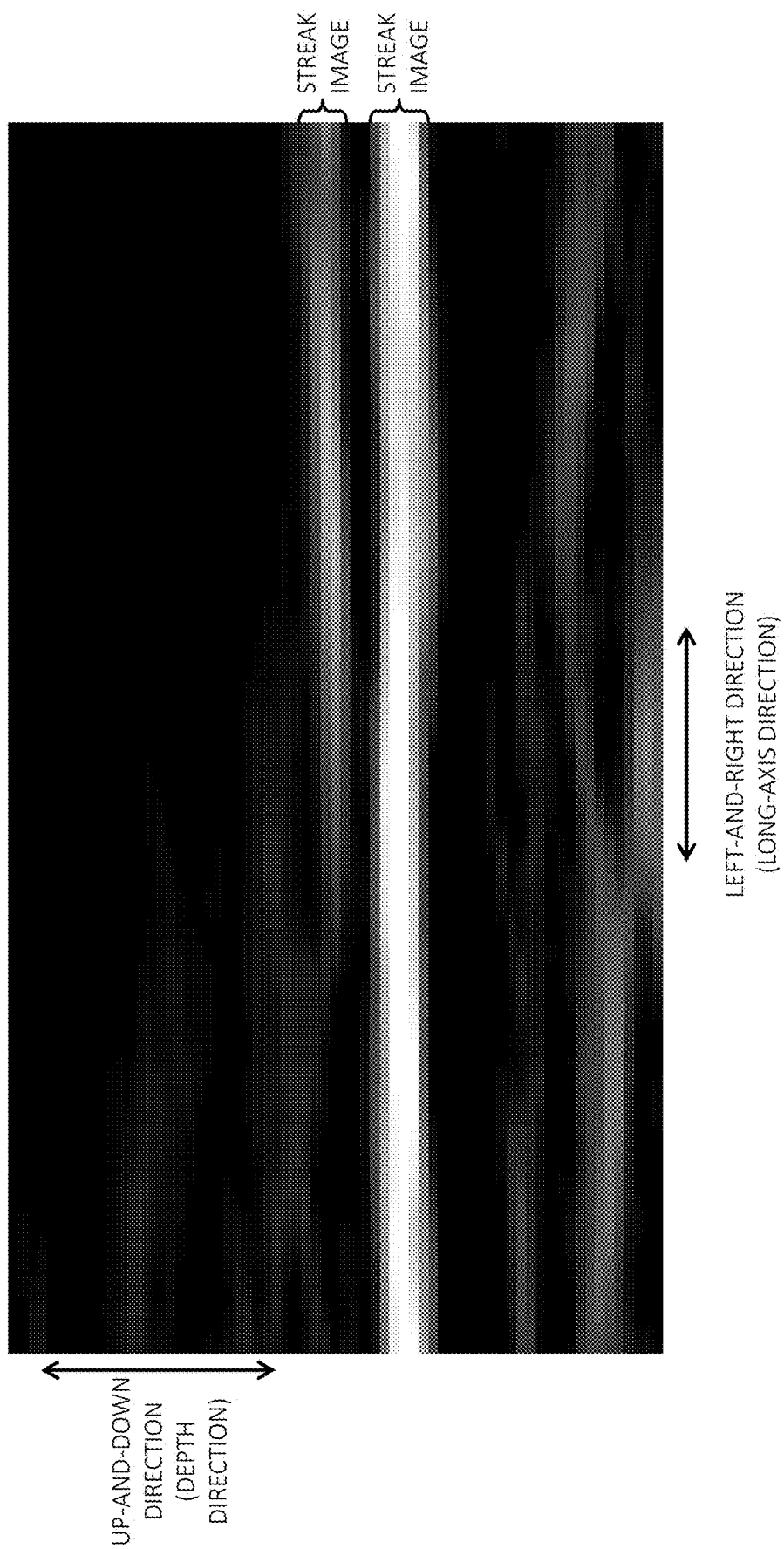
FIG. 4 is a diagram showing a specific example of an ultrasound image in which a streak image is enhanced.

FIG. 4 is a diagram showing a specific example of an ultrasound image in which the streak image is enhanced. FIG. 4 shows an image visualizing filter output values of the two-dimensional filter related to all pixels in the region of interest (ROI) which is set for the posterior wall of the blood vessel. Specifically, a grayscale image is shown in which pixels having smaller filter output values are represented with lower brightnesses (brightness near black) and pixels having higher filter output values are represented with higher brightnesses (brightness near white). With the use of the two-dimensional filter of FIG. 3, the image of FIG. 4 can be obtained in which the streak image near the tunica in the blood vessel wall is enhanced without fine noise being enhanced.

The trace line candidate extractor 40 extracts a plurality of trace line candidates which are candidates for the tunica boundaries of the blood vessel in the ultrasound image in which the streak image is enhanced. The trace line candidate extractor detects, for example, in the image shown in FIG. 4, a maxima position (peak position) of the filter output value for each line formed by a plurality of pixels arranged in one line in the up-and-down direction (depth direction). That is, a position, on each line where the filter output value changes from increasing to decreasing is detected. In some cases, a plurality of maxima positions (peak positions) may be detected on one line.

Figure 5:
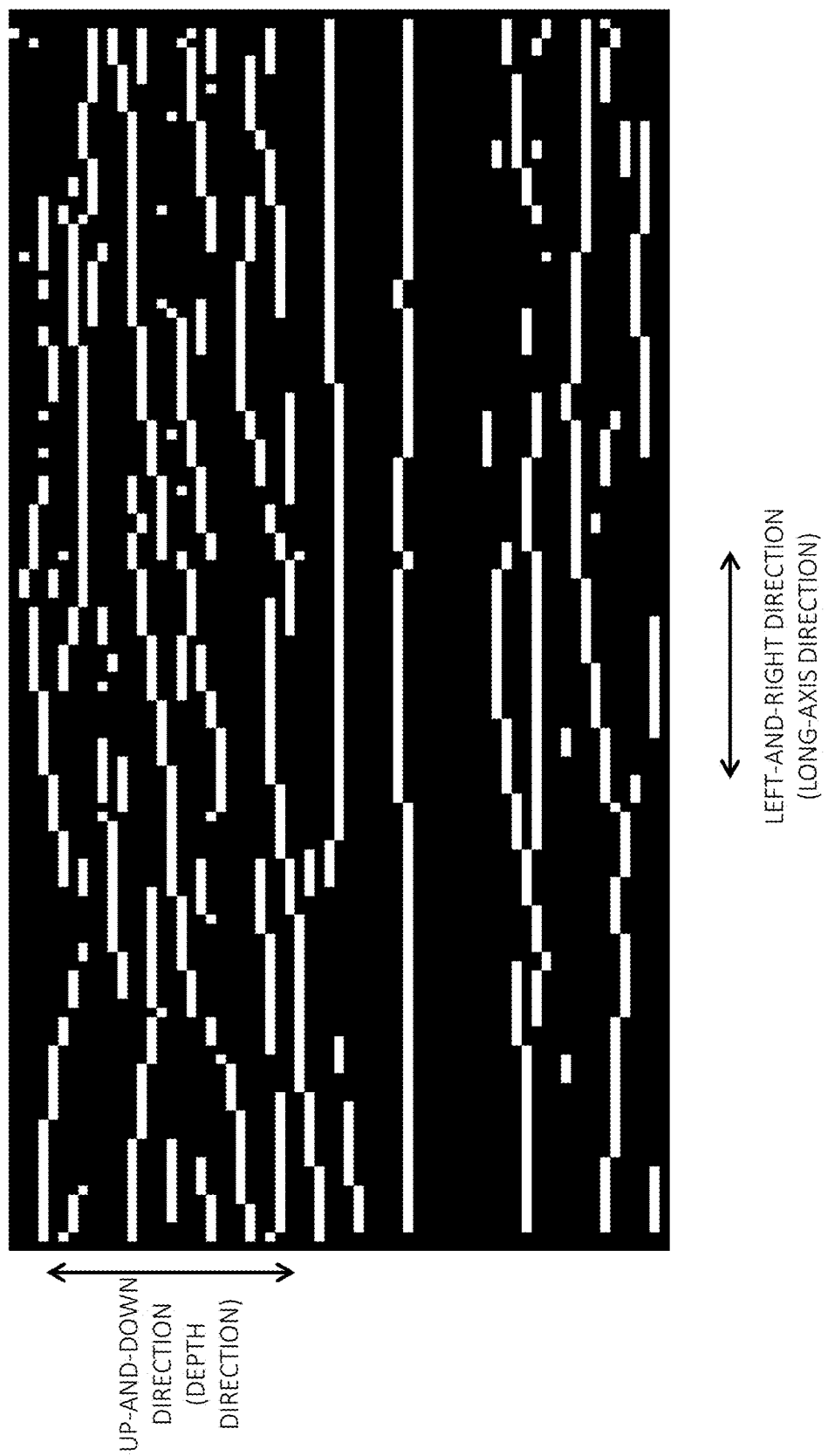
FIG. 5 is a diagram showing a specific example of a plurality of trace line candidates.

FIG. 5 is a diagram showing a specific example of the plurality of trace line candidates. FIG. 5 shows a binarized image in which, in the image of FIG. 4, the plurality of pixels corresponding to the maxima positions detected on a plurality of lines are represented with a high brightness (white) and pixels other than the maxima positions are represented by a low brightness (black). In the image of FIG. 5, each trace line candidate is formed from a plurality of pixels of high brightness continuous by eight-nearby connection (connection with eight pixels adjacent at upper, lower, left, right, and diagonal positions). The image of FIG. 5 includes a plurality of trace line candidates of various lengths. For the plurality of extracted trace line candidates, labeling is executed. That is, identification information (such as numbers) is correlated to each trace line candidate, which differs from those of the other trace line candidates.

The trace line selector 50 selects two trace lines corresponding to the intima inner side boundary and the media-adventitia boundary of the blood vessels from among the plurality of trace line candidates, based on an evaluation value related to continuity, obtained for each of the trace line candidates. The trace line selector 50 calculates, for each trace line candidate, an accumulated value accumulating the output values of the two-dimensional filter related to the plurality of pixels of the trace line candidate, and selects, as two trace lines corresponding to the intima inner side boundary and the media-adventitia boundary of the blood vessel, two trace line candidates from the largest of the accumulated value from among the plurality of trace line candidates.

Figure 6:
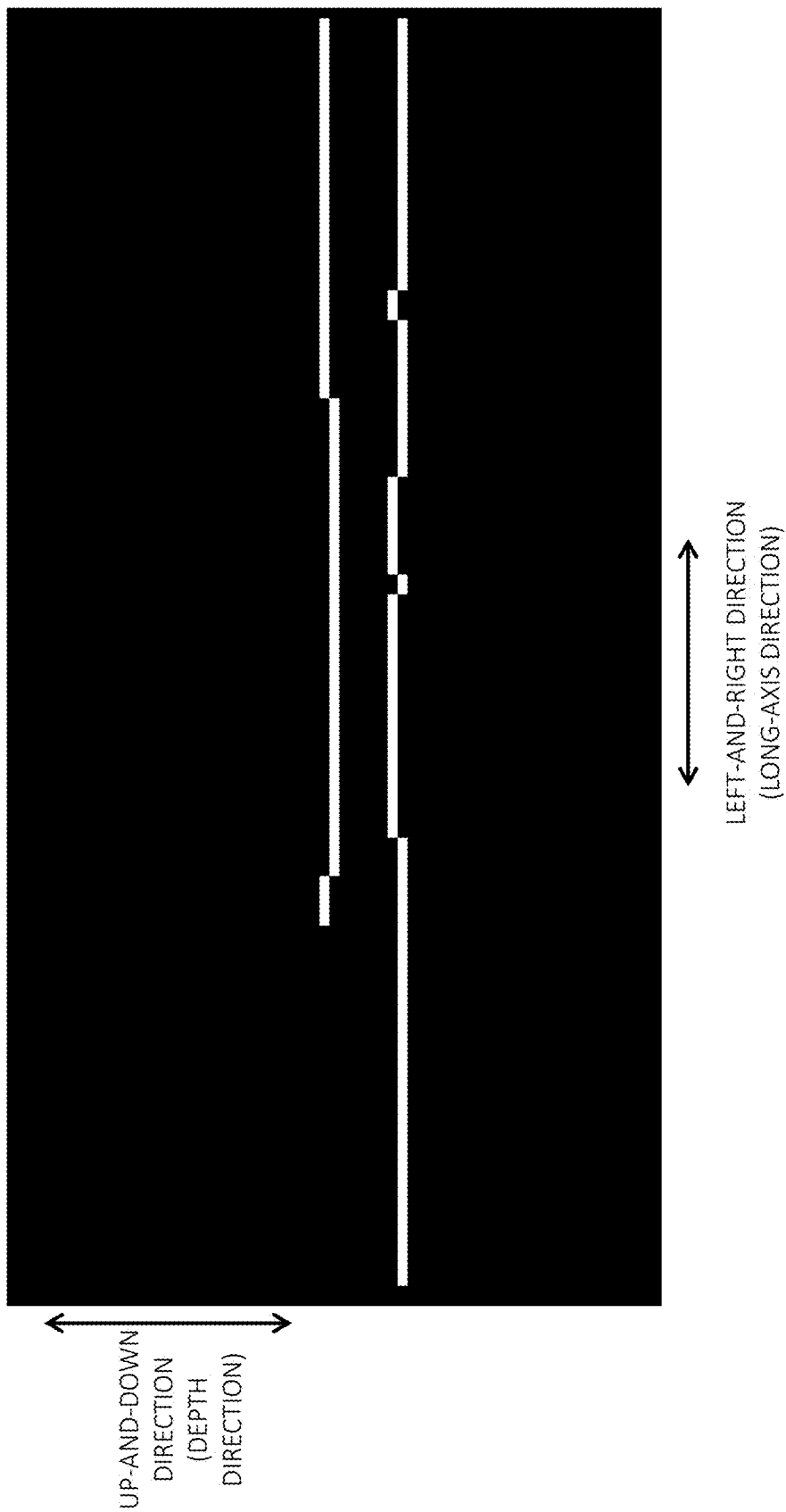
FIG. 6 is a diagram showing a specific example of two selected trace lines.

FIG. 6 is a diagram showing a specific example of the two selected trace lines. FIG. 6 shows two trace lines selected from the plurality of trace line candidates shown in FIG. 5. That is, of the plurality of trace line candidates shown in FIG. 5, FIG. 6 shows two trace line candidates from the largest of the accumulated value of the output value of the two-dimensional filter.

Because the region of interest (ROI) is set on the posterior wall of the blood vessel, of the two selected trace line candidates, an upper (at a shallower side) trace line candidate is identified as a trace line corresponding to the intima inner side boundary, and a lower (at a deeper side) trace line candidate is identified as a trace line corresponding to the media-adventitia boundary. Alternatively, when the region of interest is set on the anterior wall of the blood vessel, the upper (at the shallower side) trace line candidate is identified as the trace line corresponding to the media-adventitia boundary, and the lower (at the deeper side) trace line candidate is identified as the trace line corresponding to the intima inner side boundary.

Further, the trace line selector 50 searches for a trace line candidate to be added to the two trace lines corresponding to the intima inner side boundary and the media-adventitia boundary. For the search, first, a distance between the two selected trace lines is calculated. For example, an average distance in the up-and-down direction (depth direction) between the two trace lines shown in FIG. 6 is calculated. Then, an additional trace line candidate is searched in a search region including positions distanced from one trace line of the two trace lines toward a side of the other trace line by the average distance.

In the specific example shown in FIG. 6, because the upper (at the shallower side) trace line; that is, the trace line corresponding to the intima inner side boundary, is disconnected at a left side region, a trace line candidate to be added as the intima inner side boundary is searched in the left side region.

Figure 7:
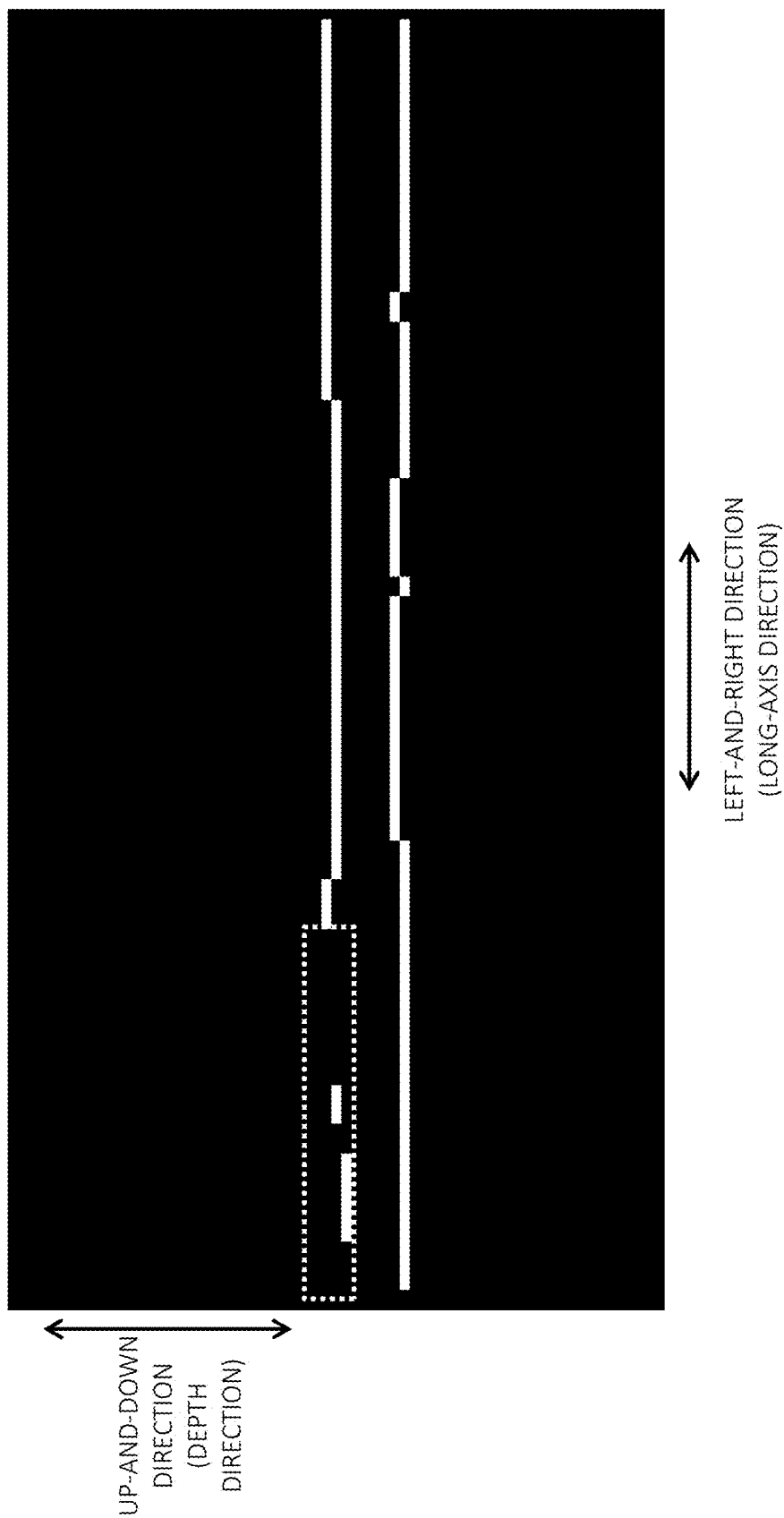
FIG. 7 is a diagram showing a search example of an additional trace line candidate.

FIG. 7 is a diagram showing an example search of the additional trace line candidate. FIG. 7 shows two trace lines (FIG. 6) corresponding to the intima inner side boundary and the media-adventitia boundary, and further shows a search region (quadrangle of a broken line) at the left side region of the trace line corresponding to the intima inner side boundary.

In the specific example of FIG. 7, the search region is set to include positions distanced from the lower trace line; that is, the trace line corresponding to the media-adventitia boundary, toward the side of the trace line corresponding to the intima inner side boundary, by the average distance described above. A size (lateral width and vertical width) of the search region may be a fixed value, or the lateral width of the search region may be adjusted according to, for example, a length, in the left-and-right direction, of the portion where the trace line is discontinuous (length of the portion where the trace line does not exist).

The trace line selector 50 searches for the additional trace line candidate in the search region. In the specific example of FIG. 7, of the plurality of trace line candidates (FIG. 5), two trace line candidates in the search region are added as trace lines corresponding to the intima inner side boundary.

The interpolation processor 60 executes an interpolation process on the two trace lines (including the additional trace line candidate) corresponding to the intima inner side boundary and the media-adventitia boundary. The interpolation processor 60 interpolates a discontinuous section of the trace line corresponding to the intima inner side boundary and the additional trace line, by a virtual line (for example, a straight line).

Figure 8:
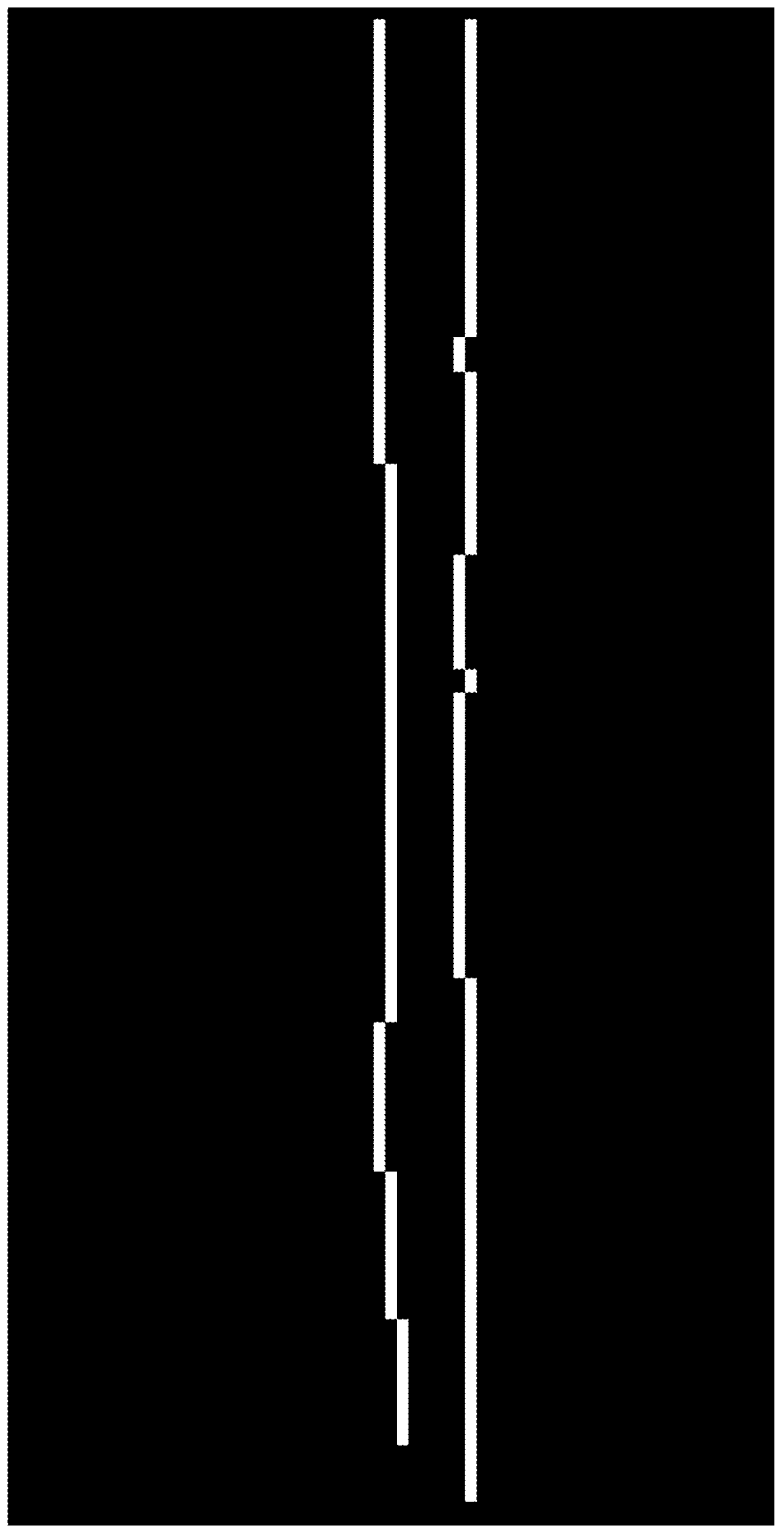
FIG. 8 is a diagram showing a specific example of a trace line to which an interpolation process is applied.

FIG. 8 is a diagram showing a specific example of the trace line to which the interpolation process is applied. FIG. 8 shows a specific example in which the discontinuous section of the trace line corresponding to the intima inner side boundary and the additional trace line shown in FIG. 7 is interpolated by the straight line. If an additional trace line is searched in relation to the trace line corresponding to the media-adventitia boundary, a discontinuous section of these trace lines is also interpolated by a virtual line (for example, a straight line). The interpolation processor 60 desirably sets only a discontinuous section of shorter than or equal to a predetermined length (for example, about 2 mm) as the interpolation target. Further, it is desirable to not execute the interpolation process of the trace line at respective ends of the region of interest (ROI). With this configuration, for example, rapid elevation (or fall) of the trace line at the ends of the region of interest can be suppressed. Further, it is desirable to execute a smoothening process to the trace line to which the interpolation process is applied.

Figure 9:
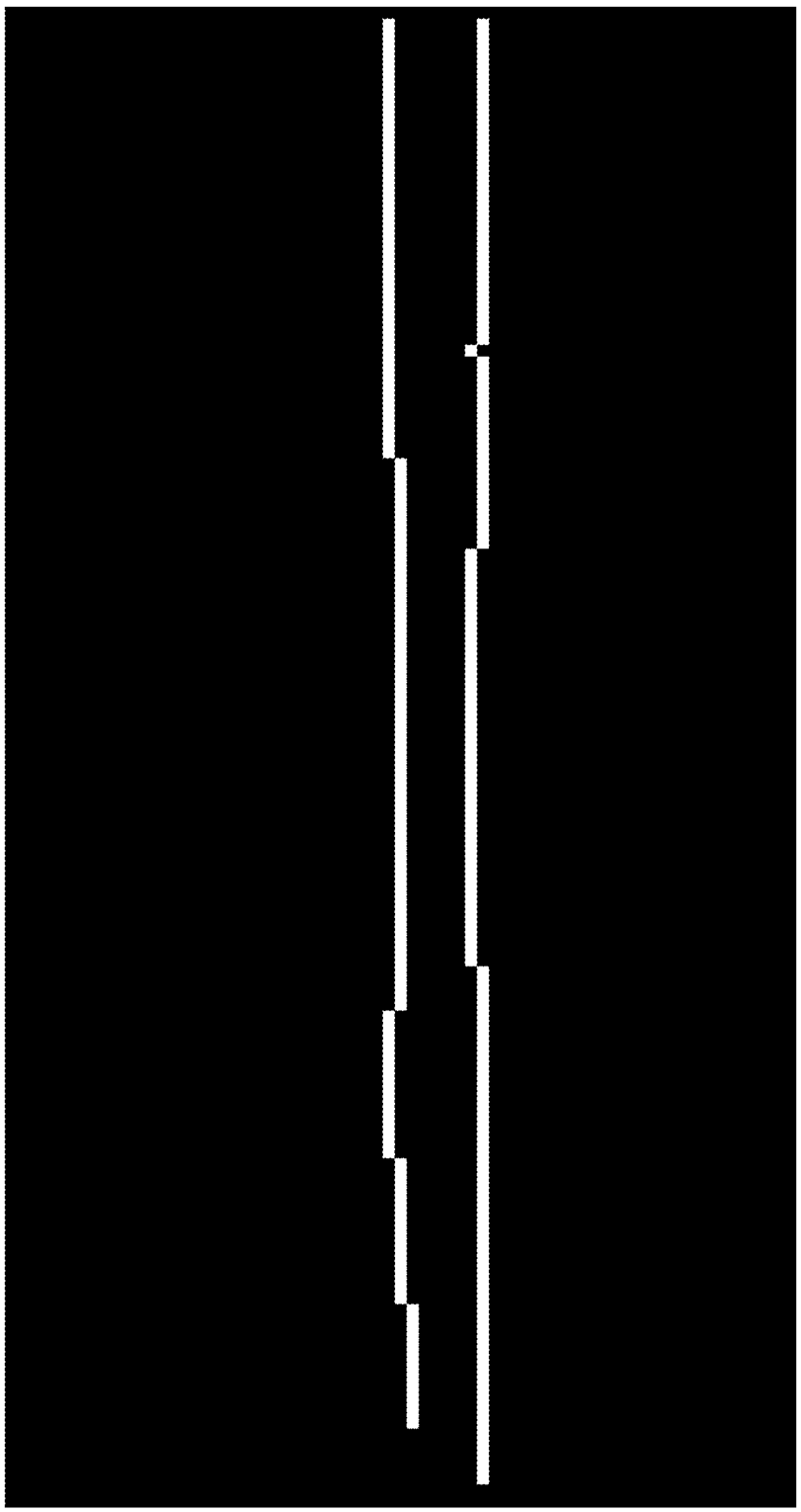
FIG. 9 is a diagram showing a specific example of a trace line to which a smoothening process is applied.

FIG. 9 is a diagram showing a specific example of a trace line to which the smoothening process is applied. FIG. 9 shows trace line after the smoothening process, in which a weighted moving average filter by a Gaussian function is applied on the trace line after the interpolation process is applied (FIG. 8). With the smoothening process, two trace lines which are relatively smooth are formed, corresponding to the original intima inner side boundary and media-adventitia boundary.

The IMT measurement unit 70 calculates the IMT measurement value based on the intima inner side boundary and the media-adventitia boundary identified by the processes from the streak image enhancement processor 30 to the interpolation processor 60. The IMT measurement unit 70 calculates, based on the two trace lines (FIG. 9) corresponding to the intima inner side boundary and the media-adventitia boundary identified in the region of interest (ROI), a distance between these two trace lines as the IMT measurement value. For example, an average of the distance between two trace lines in the region of interest is set as the IMT measurement value.

The display processor 80 forms a display image in the IMT measurement based on the cross-sectional data (image data of the ultrasound image) obtained from the image former 20 and the IMT measurement value obtained from the IMT measurement unit 70. The IMT measurement value is displayed, for example, by numerical values, graphs, or the like. The display processor 80 may also display the extraction result of the two trace lines used for the IMT measurement.

Figure 10:
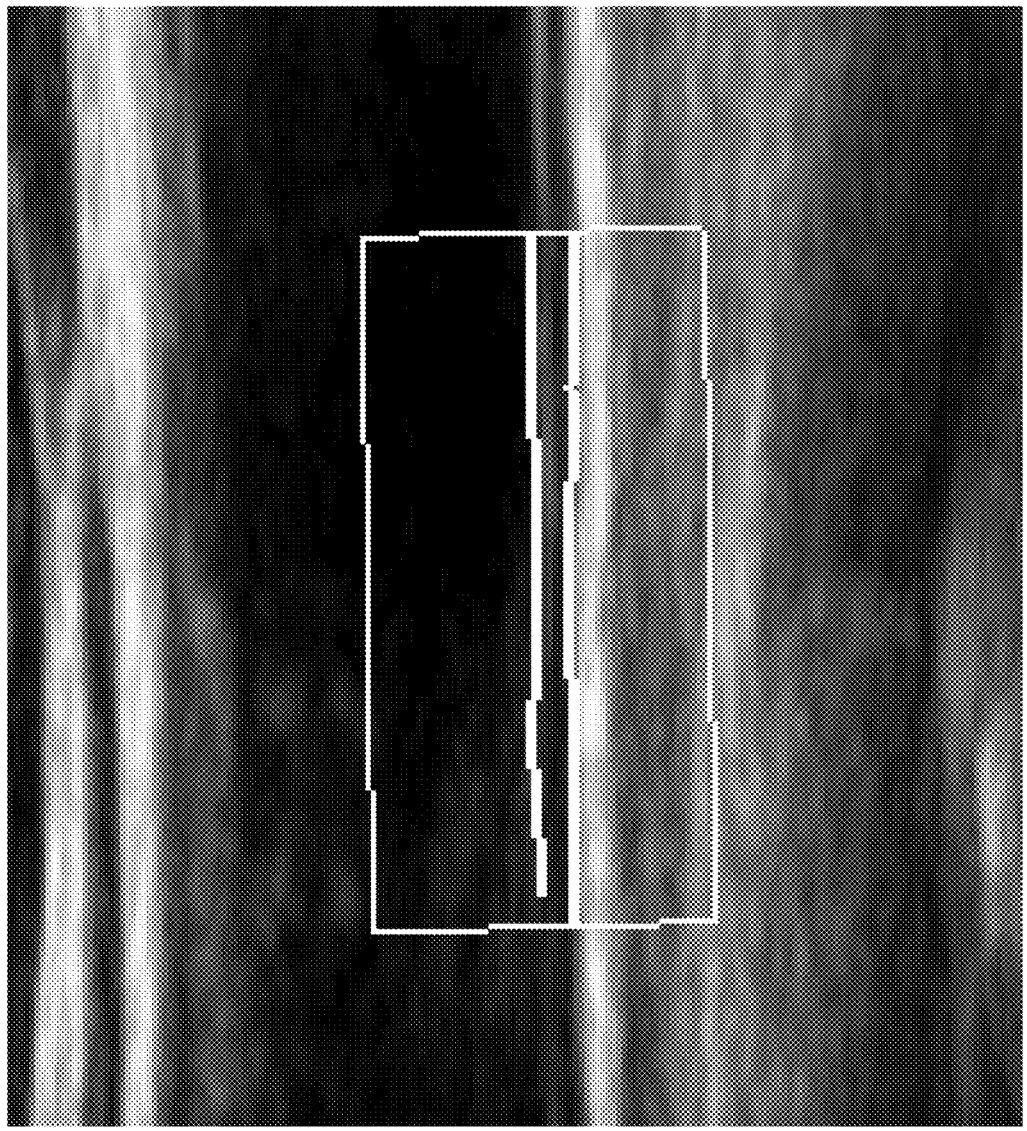
FIG. 10 is a diagram showing a specific example of a display image displaying two trace lines.

FIG. 10 is a diagram showing a specific example of the display image displaying the two trace lines. The display processor 80 forms the display image displaying, in the ultrasound image showing the long-axis cross section of the blood vessel obtained from the image former 20, the region of interest which is set by the ROI setter 22, and the two trace lines corresponding to the intima inner side boundary and the media-adventitia boundary identified by the processes from the streak image enhancement processor 30 to the interpolation processor 60.

An embodiment of the present disclosure has been described. The above-described embodiment, however, is merely exemplary in every aspect, and does not limit the scope of the present disclosure thereto. The present disclosure includes all modifications and changes within the scope and spirit of the present disclosure.

REFERENCE SIGNS LIST

10 PROBE; 12 TRANSMISSION AND RECEPTION UNIT; 20 IMAGE FORMER; 22 ROI SETTER; 30 STREAK IMAGE ENHANCEMENT PROCESSOR; 40 TRACE LINE CANDIDATE EXTRACTOR; 50 TRACE LINE SELECTOR; 60 INTERPOLATION PROCESSOR; 70 IMT MEASUREMENT UNIT; 80 DISPLAY PROCESSOR; 82 DISPLAY; 90 OPERATION DEVICE; 100 CONTROLLER.

The invention claimed is:

1. An ultrasound diagnostic apparatus comprising:
   an enhancement processor that enhances, in an ultrasound image showing a cross section of a blood vessel, a streak image corresponding to a long-axis direction of the blood vessel by a process using a two-dimensional filter which is longer in, the long-axis direction than a short-axis direction of the blood vessel;
   a candidate extractor that extracts a plurality of trace line candidates which are candidates of a tunica boundary of the blood vessel in the ultrasound image in which the streak image is enhanced, based on an output value of the two-dimensional filter; and
   a boundary selector that selects two trace lines corresponding to an intima inner side boundary and a media-adventitia boundary of the blood vessel from among the plurality of trace line candidates, based on an evaluation value related to continuity, obtained for each of the trace line candidates.

2. The ultrasound diagnostic apparatus according to claim 1, wherein
   the enhancement processor enhances, by a process using the two-dimensional filter which is tilted at a plurality of angles with respect to the long-axis direction of the blood vessel, the streak image corresponding to the plurality of angles.

3. The ultrasound diagnostic apparatus according to claim 2, wherein
   a length of the two-dimensional filter in the short-axis direction is shorter than a distance from the intima inner side boundary of the blood vessel to the media-adventitia boundary.

4. The ultrasound diagnostic apparatus according to claim 2, wherein
   the candidate extractor identifies, in the ultrasound image in which the streak image is enhanced, a plurality of maxima pixels in which the output value of the two-dimensional filter is a maximum, and connects a plurality of the maxima pixels which are in an adjacent relationship, to form each of the trace line candidates.

5. The ultrasound diagnostic apparatus according to claim 2, wherein
   the boundary selector sets, as the evaluation value and for each of the trace line candidates, an accumulated value in which the output values of the two-dimensional filter related to a plurality of pixels of the trace line candidate are accumulated, and selects, from among the plurality of trace line candidates, two trace line candidates from the largest of the accumulated value as two trace lines corresponding to the intima inner side boundary and the media-adventitia boundary of the blood vessel.

6. The ultrasound diagnostic apparatus according to claim 2, wherein
   a distance between the two trace lines which are selected is calculated, and, in a search region including a position distanced from one trace line of the two trace lines toward a side of the other trace line by the distance, at least one trace line candidate to be added to the other trace line is searched from among the plurality of trace line candidates.

7. The ultrasound diagnostic apparatus according to claim 1, wherein
   a length of the two-dimensional filter in the short-axis direction is shorter than a distance from the intima inner side boundary of the blood vessel to the media-adventitia boundary.

8. The ultrasound diagnostic apparatus according to claim 7, wherein
   the candidate extractor identifies, in the ultrasound image in which the streak image is enhanced, a plurality of maxima pixels in which the output value of the two-dimensional filter is a maximum, and connects a plurality of the maxima pixels which are in an adjacent relationship, to form each of the trace line candidates.

9. The ultrasound diagnostic apparatus according to claim 7, wherein
   the boundary selector sets, as the evaluation value and for each of the trace line candidates, an accumulated value in which the output values of the two-dimensional filter related to a plurality of pixels of the trace line candidate are accumulated, and selects, from among the plurality of trace line candidates, two trace line candidates from the largest of the accumulated value as two trace lines corresponding to the intima inner side boundary and the media-adventitia boundary of the blood vessel.

10. The ultrasound diagnostic apparatus according to claim 7, wherein
    a distance between the two trace lines which are selected is calculated, and, in a search region including a position distanced from one trace line of the two trace lines toward a side of the other trace line by the distance, at least one trace line candidate to be added to the other trace line is searched from among the plurality of trace line candidates.

11. The ultrasound diagnostic apparatus according to claim 1, wherein
    the candidate extractor identifies, in the ultrasound image in which the streak image is enhanced, a plurality of maxima, pixels in which the output value of the two-dimensional filter is a maximum, and connects a plurality of the maxima pixels which are in an adjacent relationship, to form each of the trace line candidates.

12. The ultrasound diagnostic apparatus according to claim 11, wherein
    the boundary selector sets, as the evaluation value and for each of the trace line candidates, an accumulated value in which the output values of the two-dimensional filter related to a plurality of pixels of the trace line candidate are accumulated, and selects, from among the plurality of trace line candidates, two trace line candidates from the largest of the accumulated value as two trace lines corresponding to the intima inner side boundary and the media-adventitia boundary of the blood vessel.

13. The ultrasound diagnostic apparatus according to claim 11, wherein
    a distance between the two trace lines which are selected is calculated, and, in a search region including a position distanced from one trace line of the two trace lines toward a side of the other trace line by the distance, at least one trace line candidate to be added to the other trace line is searched from among the plurality of trace line candidates.

14. The ultrasound diagnostic apparatus according to claim 1, wherein
the boundary selector sets, as the evaluation value and for each of the trace line candidates, an accumulated value in which the output values of the two-dimensional filter related to a plurality of pixels of the trace line candidate are accumulated, and selects, from among the plurality of trace line candidates, two trace line candidates from the largest of the accumulated value as two trace lines corresponding to the intima inner side boundary and the media-adventitia boundary of the blood vessel.

15. The ultrasound diagnostic apparatus according to claim 14, wherein
a distance between the two trace lines which are selected is calculated, and, in a search region including a position distanced from one trace line of the two trace lines toward a side of the other trace line by the distance, at least one trace line candidate to be added to the other trace line is searched from among the plurality of trace line candidates.

16. The ultrasound diagnostic apparatus according to claim 1, wherein
a distance between the two trace lines which are selected is calculated, and, in a search region including a position distanced from one trace line of the two trace lines toward a side of the other trace line by the distance, at least one trace line candidate to be added to the other trace line is searched from among the plurality of trace line candidates.

\* \* \* \* \*